(12) United States Patent
Sutton

(10) Patent No.: US 7,081,113 B2
(45) Date of Patent: Jul. 25, 2006

(54) HELICAL PROBE

(75) Inventor: Jeffrey Sutton, Medway, MA (US)

(73) Assignee: Depuy Acromed, Inc., Raynham, MA (US)

(*) Notice: Subject to any disclaimer, the term of this patent is extended or adjusted under 35 U.S.C. 154(b) by 86 days.

(21) Appl. No.: 10/607,902

(22) Filed: Jun. 26, 2003

(65) Prior Publication Data
US 2004/0267251 A1    Dec. 30, 2004

(51) Int. Cl.
*A61B 18/18* (2006.01)
*A61B 8/14* (2006.01)

(52) U.S. Cl. .................. 606/27; 606/41; 600/462

(58) Field of Classification Search ........... 606/1–52, 606/192, 194; 607/88–107, 115; 600/435, 600/437, 464, 439, 462; 604/508–510, 96.01
See application file for complete search history.

(56) References Cited

U.S. PATENT DOCUMENTS

| | | | |
|---|---|---|---|
| 4,762,130 A * | 8/1988 | Fogarty et al. ............. | 606/159 |
| 4,955,377 A | 9/1990 | Lennox et al. | |
| 5,411,509 A * | 5/1995 | Hilal ........................... | 606/159 |
| 5,458,596 A | 10/1995 | Lax et al. | |
| 5,569,242 A | 10/1996 | Lax et al. | |
| 5,944,687 A * | 8/1999 | Benett et al. ................. | 604/22 |
| 6,035,238 A | 3/2000 | Ingle et al. | |
| 6,071,280 A | 6/2000 | Edwards et al. | |
| 6,179,836 B1 | 1/2001 | Eggers et al. | |
| 6,254,626 B1 * | 7/2001 | Dobak et al. ............... | 607/105 |
| 6,280,441 B1 | 8/2001 | Ryan | |
| 6,314,963 B1 * | 11/2001 | Vaska et al. ................ | 128/898 |
| 6,427,089 B1 * | 7/2002 | Knowlton ................... | 607/101 |
| 6,533,804 B1 * | 3/2003 | Dobak et al. ............... | 607/105 |
| 6,895,267 B1 * | 5/2005 | Panescu et al. ............. | 600/424 |
| 2003/0014127 A1 | 1/2003 | Talja et al. | |

FOREIGN PATENT DOCUMENTS

WO    02/28302 A1    11/2002

* cited by examiner

*Primary Examiner*—Michael Peffley
(74) *Attorney, Agent, or Firm*—Thomas M. DiMauro

(57) ABSTRACT

The present invention relates to a therapeutic probe adapted to aid in the insertion and navigation of the probe into delicate tissue structures, and to provide protection of adjacent tissue structures.

9 Claims, 5 Drawing Sheets

HELICAL PROBE

BACKGROUND OF THE INVENTION

In an effort to reduce back pain through early intervention techniques, many investigators have focused upon heating a portion of the annulus fibrosus.

Some investigators have provided such heat by first inserting a probe into the nucleus pulposus section of an intervertebral disc and then heating the annulus fibrosus portion of the disc from that location.

Although this technique may provide therapy to the annulus fibrosus, it also requires puncturing the annulus fibrosus in another location, thereby increasing the risk of a later herniation.

U.S. Pat. No. 5,569,242 ("Lax") discloses a radiofrequency (RF) probe for heating the exterior wall of the annulus fibrosus of a herniated disc. See FIG. 23 of Lax. Lax further discloses that the probe may include an insulator positioned between the electrode and adjacent tissue for protecting the adjacent tissue from heat produced by the electrode. See FIG. 9 of Lax. Lax further discloses a probe having a configuration wherein the electrode is spaced from the tissue to be treated. See FIG. 10 of Lax. Although Lax further discloses a roller element electrode having projections, Lax does not disclose any function of such projections. See FIG. 18 of Lax.

Lax does not disclose a means for aiding the insertion of the probe. Lax does not disclose a probe having an inflatable portion positioned between the target tissue and the electrode.

PCT Published Patent Application No. WO 02/28302 ("Brett") also discloses a thermal therapy device adapted to exteriorly treat the intervertebral disc. One embodiment disclosed by Brett contains a distal end that is smoothly rounded for reaching the injury site without snagging and is thinner to provide easy insertion between tissue layers. Another embodiment contains a wedged portion that is expandable to protect adjacent non-target tissue. The FIG. 12 embodiment of Brett contains a malleable energy application region 350 that appears to allow the surface of the device through which energy flows to conform to the target tissue surface.

In sum, the devices disclosed by Lax and Brett are configured and adapted for treating an intervertebral disc from outside the disc, and each recognizes a need to protect adjacent or target tissue from overheating.

SUMMARY OF THE INVENTION

The present inventor has recognized additional needs in devices adapted for exterior treatment of the intervertebral disc, and has developed devices that would be beneficial in providing features addressing those needs. These additional needs include but are not limited to a) navigation into difficult and sensitive anatomies, and b) protection of non-target adjacent structures from non-heating threats.

First, the present inventor has recognized that it would be advantageous to treat the disc from its posterior aspect, and that locating the device at that site would entail its very careful navigation between the tissue of the disc and the spinal cord. One issue associated with this navigation is the need to insure the integrity of the spinal cord during this navigation. Therefore, it would be advantageous to provide the device with a soft surface against the spinal cord. Accordingly, in one embodiment of the present invention, there is provided a therapeutic probe adapted for insertion between a target tissue and an adjacent tissue, the probe comprising:
  a) a proximal end portion,
  b) a distal end portion,
  c) a longitudinal portion located between the proximal and distal end portions, the longitudinal portion having an axial cross-section defining top and bottom surfaces, a front side surface and a back side surface,
  d) therapeutic agent-delivering means provided in the longitudinal portion and adapted to deliver a therapeutic agent through the front side surface to the target tissue, wherein the back side surface of the longitudinal portion is adapted to conform to a contour of the adjacent tissue.

In some embodiments, thereof, the soft surface is provided in the form of a soft thread. The threaded nature of the device further provides the clinician with not only some mechanical advantage that reduces the insertion force required to be supplied by the clinician, but also with increased control over device insertion. Therefore, in accordance with the invention, there is provided a therapeutic probe adapted for insertion between a target tissue and an adjacent tissue, the probe comprising:
  a) a proximal end portion,
  b) a distal end portion,
  c) a longitudinal portion located between the proximal and distal end portions, the longitudinal portion having an axial cross-section defining an outer surface, and
  d) therapeutic-agent delivering means provided in the longitudinal portion and adapted to deliver a therapeutic agent through the outer surface to the target tissue, wherein the outer surface of the longitudinal portion comprises a threadform.

Second, navigation to the posterior aspect entails the distal displacement of tissue. One issue associated with such displacement is the trauma to the tissues that are displaced. Therefore, it would be advantageous to provide a device with a soft distal end. Accordingly, in one aspect of the present invention there is provided a therapeutic probe adapted for insertion between a target tissue and an adjacent tissue, the probe comprising:
  a) a proximal end portion,
  b) a distal end portion,
  c) a longitudinal portion located between the proximal and distal end portions, and
  d) therapeutic-agent delivering means provided in the longitudinal portion and adapted to deliver a therapeutic agent to the target tissue, wherein the distal end portion is adapted to conform to a contour of the adjacent tissue.

Third, navigation to the posterior aspect can be aided by providing a distally located radio-opaque marker. This marker will help the clinician suitably locate the distal end of the device under fluoroscopy, and thereby insure the device is not overextended into the patient. Accordingly, in one aspect of the present invention there is provided a therapeutic probe adapted for insertion between a target tissue and an adjacent tissue, the probe comprising:
  a) a proximal end portion,
  b) a distal end portion,
  c) a longitudinal portion located between the proximal and distal end portions, and
  d) therapeutic agent-delivering means provided in the longitudinal portion and adapted to deliver a therapeutic agent to the target tissue, wherein the distal end portion comprises a radio-opaque contrast agent.

Fourth, the present inventor has recognized that, even when navigation to the desired site is accomplished, the device may nonetheless be subject to either in vivo or ex vivo forces providing the potential for retropulsion. Therefore, it would be advantageous to provide a device having means for resisting retropulsion. In one embodiment thereof, the device contains expandable devices (such as a balloon) that is expanded after the device is desirably located to keep the device in its desired location. Accordingly, in one aspect of the present invention, there is provided a therapeutic probe adapted for insertion between a target tissue and an adjacent tissue, the probe comprising:
   a) a proximal end portion,
   b) a distal end portion,
   c) a longitudinal portion located between the proximal and distal end portions, the longitudinal portion having an axial cross-section defining an outer surface,
   d) therapeutic agent-delivering means provided in the longitudinal portion and adapted to deliver a therapeutic agent through the front side surface to the target tissue, wherein the outer surface of the longitudinal portion comprises a retropulsion resistance means.

In some embodiments thereof, the back side surface of the probe has a positioning balloon having a concave contour for easily conforming to the convex surface of the adjacent spinal cord.

In some embodiments thereof, the expandable balloon is filled with a radio-opaque contrast agent that allows the clinician to monitor the placement of the device by x-ray.

Fifth, the present inventor has recognized other in vivo or ex vivo forces may provide the potential for torquing the probe after it has reached its desired location. Therefore, it would be advantageous to provide a device having means for resisting torquing. In one embodiment thereof, the device has an axial cross-section in which the opposing surfaces contacting the disc and spinal cord are of a dimension greater than the corresponding dimensions of the upper and lower surfaces (i.e., the height/width ratio of the cross-section is greater than 1. Accordingly, in one aspect of the present invention, there is provided a therapeutic probe adapted for insertion between a target tissue and an adjacent tissue, the probe comprising:
   a) a proximal end portion,
   b) a distal end portion,
   c) a longitudinal portion located between the proximal and distal end portions, the longitudinal portion having an axial cross-section defining top and bottom surfaces, a front side surface and a back side surface,
   d) therapeutic agent-delivering means provided in the longitudinal portion and adapted to deliver a therapeutic agent through the front side surface to the target tissue, wherein the front side surface of the longitudinal portion has a front side dimension defining a height, the top side surface of the longitudinal portion has a top side dimension defining a width, and the front side dimension is greater than the top side dimension so that the height/width ratio is greater than 1.

Sixth, when the therapeutic agent delivered by the device is ultrasound, it would be advantageous to provide a fluid that couples with the ultrasound. Brett does not recognize any need for such a coupling fluid. Although the FIG. 10 embodiment of Lax provides an electrolytic dam, the electrolyte is not contained within the device, and so is subject to leakage. It would be advantageous to provide a device for therapeutically delivering ultrasound energy having a contained ultrasound coupling agent. Accordingly, in one aspect of the present invention, there is provided a therapeutic probe adapted for insertion between a target tissue and an adjacent tissue, the probe comprising:
   a) a proximal end portion,
   b) a distal end portion,
   c) a longitudinal portion located between the proximal and distal end portions, the longitudinal portion having an axial cross-section defining top and bottom surfaces, a front side surface and a back side surface,
   d) ultrasound-delivering means provided in the longitudinal portion and adapted to deliver ultrasound through the front side surface to the target tissue, wherein the longitudinal portion contains an ultrasound-coupling agent located adjacent to the front side surface.

In addition, when the therapeutic agent delivered by the device is ultrasound, it would be advantageous to provide a device having multiple transducers. The provision of multiple transducers would provide the clinician with both imaging and depth-focusing capabilities. Accordingly, in one aspect of the present invention, there is provided a therapeutic probe adapted for insertion between a target tissue and an adjacent tissue, the probe comprising:
   a) a proximal end portion,
   b) a distal end portion,
   c) a longitudinal portion located between the proximal and distal end portions, the longitudinal portion having an axial cross-section defining top and bottom surfaces, a front side surface and a back side surface,
   d) ultrasound-delivering means provided in the longitudinal portion and adapted to deliver ultrasound through the front side surface to the target tissue, wherein the ultrasound-delivering means comprises a plurality of ultrasound transducers.

DETAILED DESCRIPTION

For the purposes of the present invention, the term "provided in" means located within or on the outer surface of the probe; a "target tissue" is the tissue into which the clincian intends to deliver the therapeutic agent; an "adjacent tissue" is the tissue adjacent the target tissue into which the clinician desires to avoid the delivery of the therapeutic agent, and the "spinal cord" includes the thecal sac.

Figure 1:
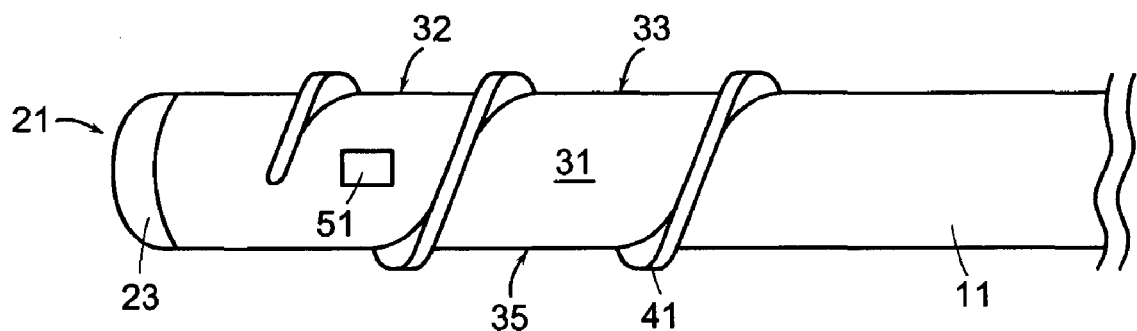
FIG. 1 presents a side view of a probe of the present invention having an inflatable threadform.
Figure 2A:
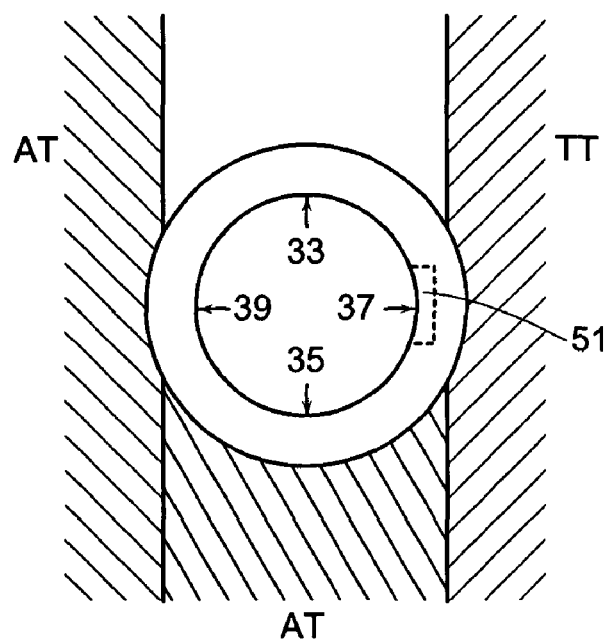
FIGS. 2a and 2b respectively present a distal end view and an above view of the probe of FIG. 1 embedded in a channel between a target tissue and adjacent tissues.
Figure 2B:
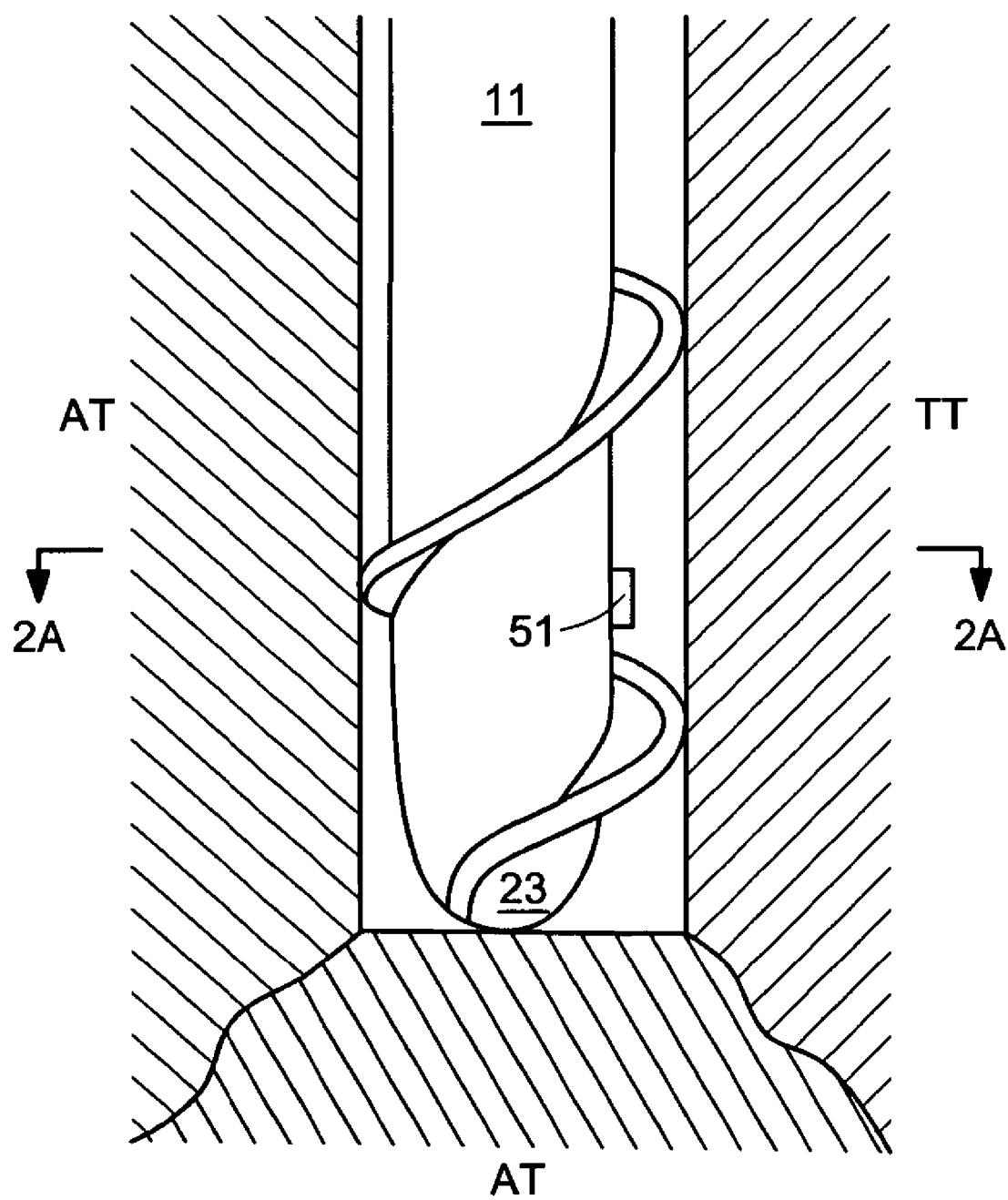

Now referring to FIGS. 1, 2a and 2b, there is provided a therapeutic probe 1 adapted for insertion between a target tissue TT and a first adjacent tissue $AT_1$, the probe comprising:
 a) a proximal end portion 11,
 b) a distal end portion 21 comprising a malleable material portion 23,
 c) a longitudinal portion 31 located between the proximal and distal end portions, the longitudinal portion having an axial cross-section defining an outer surface 32 defining:
  a top surface 33,
  a bottom surface 35,
  a front side surface 37, and
  a back side surface 39 adapted to conform to a contour C of the adjacent tissue, and
 d) therapeutic agent-delivering means 51 provided in the longitudinal portion and adapted to deliver a therapeutic agent through the front side surface to the target tissue, wherein the outer surface of the longitudinal portion comprises a helical balloon 41 forming a threadform.

The helical shaped balloon of FIG. 1 may be made of either compliant or non-complaint materials fabricated into an expandable shape having an expandable shell and an inlet. The shell may be made of suitable polymers. When inflated or expanded, the threadform so produced can aid in the insertion of the probe between the intervertebral disc and the spinal cord by simply rotating the probe in the desired manner during insertion. Once the probe is inserted between the spinal cord and the disc, the expanded balloon provides a "stand-off" or spacing between a) the therapeutic agent delivery means, and b) each of the spinal cord and disc. The "stand-off" attribute of the probe prevents or mitigates potentially harmful effects upon the tissues due to either probe insertion or operation. The "stand off" may be accomplished by either a) the physical distance created by the balloon between the tissues and the therapeutic agent delivery means, or by special properties provided by the substance filling the balloon, or by both. Preferably, the balloon has no sharp edges in its expanded form.

In preferred embodiments using ultrasound, the helical balloon and ultrasound transducer are positioned so that the ultrasound is delivered through the balloon, thereby eliminating any air gap between the target tissue and the ultrasound transducer.

In addition to the above-noted features, the probe provided in FIG. 1 also provides a more uniform force during insertion and a more controlled insertion (due to the threadform nature of the outer surface). It also provides a mechanical advantage that produces a higher or increased force (also due to the threadform nature of the outer surface). It also may be deflated and therefore more easily removed from the insertion location (owing to the decreased profile of the deflated state).

Although a helical shape provides the above-noted advantages, it may be more advantageous in some situations to provide other special shapes or impart a special geometry to the outer surface of the probe. For example, in some embodiments, it may be advantageous to provide a plurality of expandable shapes upon the outer surface of the catheter.

Figure 3:
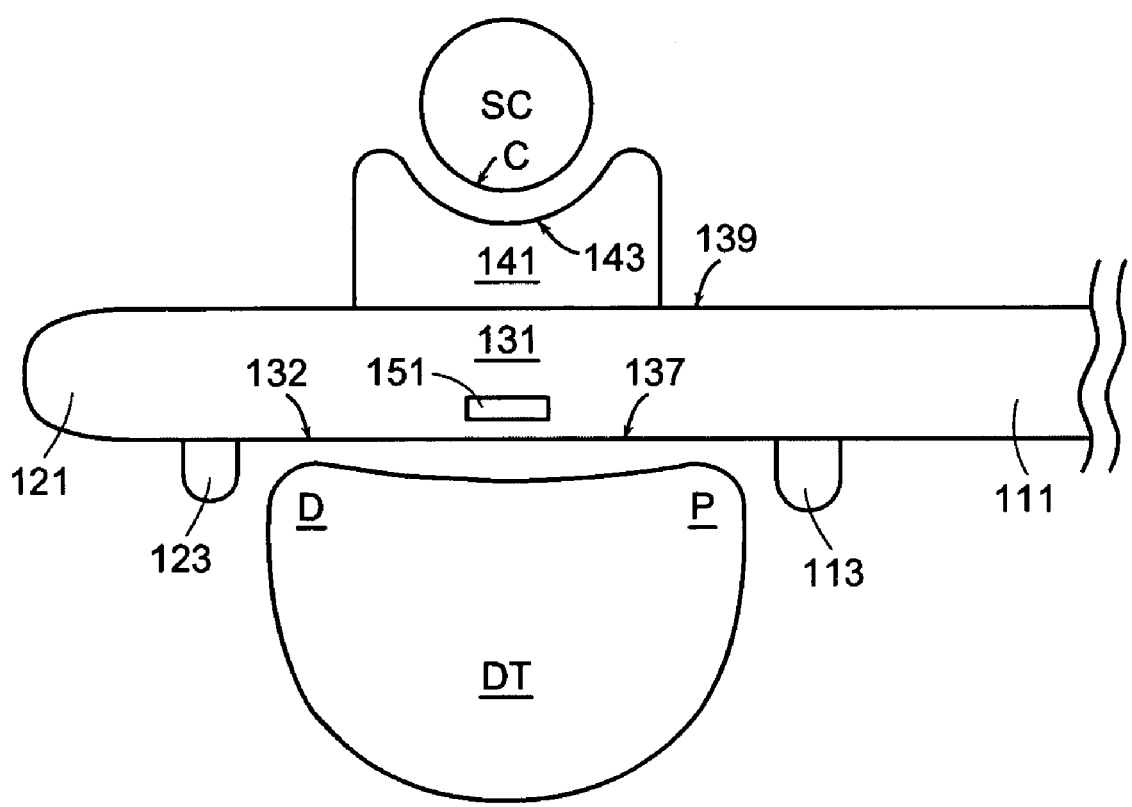
FIG. 3 presents a side view of a probe of the present invention having an inflatable proximal and distal balloons disposed on the front side of probe, and an intermediate inflatable balloon disposed on the backside of the probe and having a concave shape.

Now referring to FIG. 3, there is provided a therapeutic probe adapted for insertion between a target disc tissue DT having a proximal end P and distal end D and an adjacent spinal cord tissue SC, the probe comprising:
 a) a proximal end portion 111 comprising a first expandable portion 113 adapted to conform to the proximal end of the disc tissue,
 b) a distal end portion 121 comprising a second expandable portion 123 adapted to conform to the distal end of the disc tissue,
 c) a longitudinal portion 131 located between the proximal and distal end portions, the longitudinal portion having an axial cross-section defining an outer surface 132 defining:
  a top surface (not shown),
  a bottom surface (not shown),
  a front side surface 137, and
  a back side surface 139 having an expandable device 141 having a concave portion 143 adapted to conform to a contour C of the spinal cord, and therapeutic agent-delivering means 151 provided in the longitudinal portion and adapted to deliver a therapeutic agent through the front side surface to the target tissue.

In this FIG. 3 embodiment, the lateral balloons function so as to maintain the axial position of the probe. They do so by essentially straddling the distal and proximal ends of the disc to be treated. In contrast, the middle balloon functions so as to provide a stand-off distance between the therapeutic agent delivery means and the spinal cord. It does so by inflation. In addition, the concave surface of the middle balloon allows it to function so as to maintain the axial position of the probe by essentially straddling the spinal cord.

In this FIG. 3 embodiment, the distal balloon is shaped, located and oriented so as to provide a stop to prevent the accidental removal or retropulsion of the probe. Likewise, the proximal balloon could provide a stop to prevent the over-insertion of the probe past a desired position. This proximal stop may also be adapted to prevent undesired movement of the probe. Each of these stops may also be adapted to provide a standoff between the remaining parts of the probe and sensitive local nerve roots.

Figure 4:
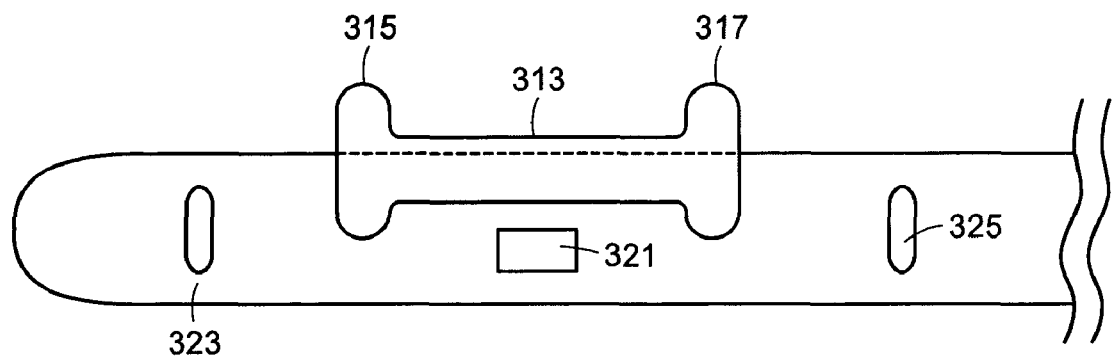
FIG. 4 presents a side view of a probe of the present invention having an inflatable proximal and distal balloons, and an intermediate inflatable balloon having a dogbone shape.

Now referring to FIG. 4, there is provided a probe of the present invention wherein the expandable device located in the longitudinal portion of the probe has a dogbone shape. The balloon comprises lower profile central region 313 extending in the longitudinal direction, a higher profile distal region 315 extending from the central region in a transverse direction, and a higher profile proximal region 317 also extending from the central region in the transverse direction. This balloon may beneficially maintain the position of a certain anatomy (such as the spinal cord) within the longitudinal region of the probe, thereby providing both protection and position maintanence.

Also provided in FIG. 4 are distal 323 and proximal 325 expandable devices, and therapeutic agent delivery means 321.

Still referring to FIG. 4, the expandable device located in the longitudinal portion of the probe also extends in the transverse direction about an arc of about 180 degrees. This extended arc provides the advantage of providing a standoff between the therapeutic agent delivery device and the adjacent tissue, and also provides a means for ascertaining proper placement under fluoroscopy when filled with radioopaque material. The 180 degree nature of the arc provides the ability to insert the device past the spinal cord with the smooth side adjacent the cord, then rotating 180 degrees once the device is in place, thereby minimizing trauma to the cord due to the deflated balloon profile.

Likewise, positioning additional of other geometrical features, such as the proximal and distal balloons as shown in FIG. 4, in other locations and orientations could provide additional benefits.

In other embodiments, the balloon of FIG. 4 can be modified so that it produces a probe wherein the distal proximal and central expandable regions of the expandable device are individually expandable. Now referring to FIG. 5, there is provided a probe having an outer surface comprising:

a) a distal balloon 413,
b) a proximal balloon 417, and
c) a central balloon 415.

Preferably, each of these balloons is placed in fluid connection with an independent lumen contained within the catheter (not shown), and each independent lumen is also in fluid connection with an inflation device attached to the handle (not shown).

The proximal balloon of this configuration may be adapted to prevent over-insertion of the probe into a channel or other body anatomy (e.g., a vertebral foramen) before inflating the distal and central expandable devices.

In addition, the proximal and distal balloons may provide other benefits, such as moving, displacing, heating, cooling or delivering drugs or fluids to nearby anatomy such as nerve roots or other structures. Likewise, the central balloon may provide multiple beneficial features such as moving, displacing, heating, cooling or delivering drugs or fluids to nearby anatomy such as the spinal cord, vertebral discs, or other structures.

Figure 5:
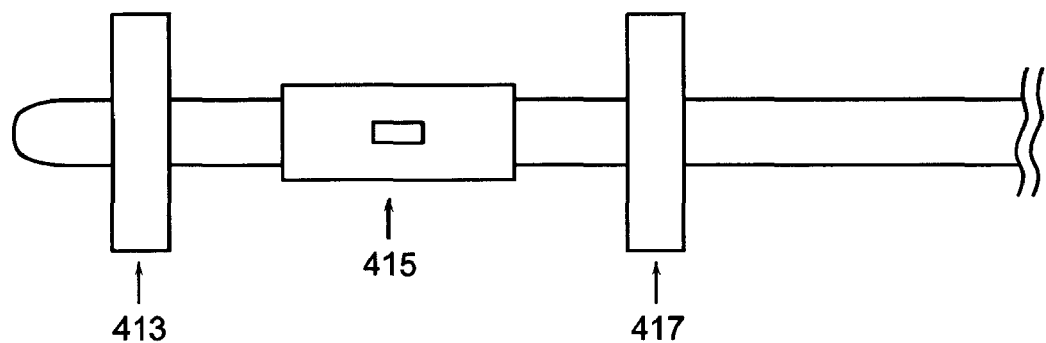
FIG. 5 presents a side view of a probe of the present invention having an inflatable proximal and distal balloons, and an intermediate inflatable balloon having a cylindrical shape.

In some embodiments, the expandable devices may also be segmented to provide a front side and a backside balloon for any or all of the distal, proximal and central balloons provided in FIG. 5. This provides the clinician with increased operative freedom. For example, the clinician may be able to heat the target tissue with the front side balloon and cool or provide stand off with adjacent tissue with the back side balloon, or vice versa. In such a segmented probe, the clinician may also be able to deliver different fluids or drugs through the segmented portions.

Preferably, the therapeutic-agent delivering means is selected from the group of energy-delivering means and drug delivery means. In some embodiments, the therapeutic-agent delivering means is an energy-delivering means, and is selected from the group consisting of ultrasound, radiofrequency (RF), microwave, diffuse light, laser light, UV light, IR light, resistive energy, and heated or cooled fluids. In some preferred embodiments, the therapeutic-agent delivering means is ultrasound energy.

When ultrasound is selected as the therapeutic-energy delivering means, the balloons will maintain intimate contact between the target tissue and the energy delivery surface (e.g., by pushing against the lateral bony walls of the spinal cord, or by being positioned directly between the target tissue and the energy delivery device (preferably an ultrasound transducer) so as to provide a means for acoustic coupling of the energy from the transducer to the target tissue. In some embodiments, the means comprises a plurality of ultrasound transducers. Providing a plurality of ultrasound transducers allows the clinician to advantageously image and focus.

In general, a conformable component has the ability to generally conform to a space into which it is delivered. In some embodiments, the conformable component slightly deforms the surface to which it conforms, but only to an extent that the conformable component provides a tight fit therewith and does not injure the surface to which it conforms.

The conformable component may take on any shape desirable for aiding navigation or protecting adjacent tissues. These shapes include a square, a dogbone, an ellipse, a round, a rectangle, or combinations thereof.

In some embodiments, the conformable component can be a material having a low modulus of compression, such as between about Shore "OO" 20 and about Shore "A" 50. Such materials include rubber, nylon, polyethylene, PET, urethane, silicones, and fluoropolymers. One especially preferred material is silicone. In some embodiments, the conformable component comprises a malleable portion comprising a foam portion, which makes the conformable portion extremely soft.

In other embodiments, the conformable component comprises an expandable device having a lumen. These expandable devices comprise an inlet in fluid connection with an expandable shell. The expandable device increases in volume when a gas or liquid is introduced through the inlet into the shell. In some embodiments, the shell is a a woven shell). In some embodiments, the shell is a balloon).

The conformable shape may be any shape suitable for either a) providing an aid to insertion of the probe's distal end into the desired body anatomy (such as the region between the spinal cord and the posterior aspect of the intervertebral disc), b) preventing the over-insertion of the probe into a sensitive region of the anatomy (for example, to limit or control the insertion of the catheter into a desired anatomy without inserting it too far into the undesired anatomy), or c) protecting, moving, dislodging, or treating certain special anatomical tissues by virtue of their intimate or proximal contact therewith upon the outer surface of the probe.

Figure 6A:
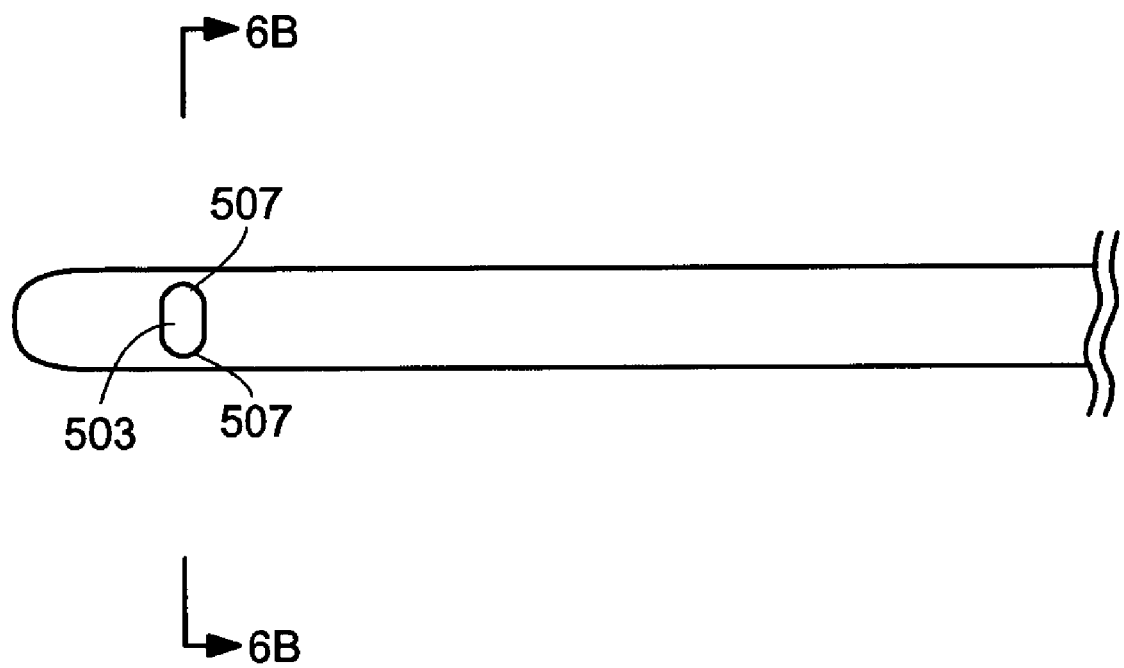
FIGS. 6a and 6b are side and end view of a probe of the present invention having a moon-like flange defining a maximal edge and a minimal edge.
Figure 6B:
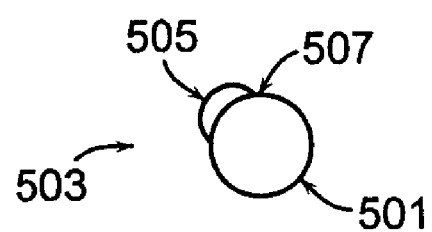

Mechanisms other than balloons may be used to achieve similar desirable shapes upon the outer surface of the probe. These shapes could be rigid or semi-rigid flanges providing the probe with a contours having a gradually increasing thickness in the distal to proximal direction. When these flanges are provided, the probe may be rotated to provide their desired orientation. For example, and now referring to FIGS. 6A and 6B, the probe 501 may a comprise i) a moon-like flange 503 defining a maximal edge 505 of the circular outer surface of the probe, as well as a leading or minimal edge 507. The advantage of providing such a moon-like flange is to provide an eccentric, gradually inclined surface feature or profile to the device that could gradually displace tissue or structures, either by linear movement of the device, or by rotation of the device, or by a combination of both linear and rotational movements. These flanges may be integral to the remainder of the outer surface of the probe, or they may be manufactured separately and then attached to the probe.

Although the present invention is adapted for providing navigation aid and tissue protection for any region of the body, preferred embodiments of the present invention are directed to probes adapted for treating the intervertebral disc from a location along the posterior aspect of the disc to be treated, and more preferably in a region directly between the spinal cord and the posterior aspect of the disc to be treated.

In such embodiments, the primary tissue to be protected by the present invention is the spinal cord. Secondary tissues which may also be protected include the dorsal nerves located in and near the intervertebral foramen. Other tissues to be protected include vertebral arteries and veins.

In some embodiments, the expandable device has a helical shape and is fit to the outer surface of the probe to define a threadform. This threadform allows the probe to be screwed into the desired location.

As noted above, the expandable bodies are expanded by the introduction of gas or liquid agents through an inlet in the expandable body and into the expandable shell. Accordingly, these fluids have a shape-creating role. However, in some embodiments, these fluids may also have special properties or characteristics that provide the probe with additional advantages.

For example, in some embodiments, the expansion fluid may be introduced into the expandable device at a temperature above body temperature. This heated expansion fluid may provide therapeutic heat to adjacent tissues.

In some embodiments, the expansion fluid may be introduced into the expandable device at a temperature below body temperature. This cooled expansion fluid may provide cooling to an energy delivery device located in the probe, thereby preventing its overheating, or to provide cooling to adjacent sensitive tissues, e.g., nerves.

In some embodiments, the expansion fluid may be a drug that is introduced into an expandable device having a selectively permeable expandable shell. This drug may be delivered through the shell and to the local tissue. In some embodiments, the permeable shell has microporosity (i.e., pores on the order of 0.01 µm–1.0 µm). In others, the permeable shell has selected macro-sized holes (i.e., holes on the order of 1 µm–10 µm) through which the drug is delivered.

Although the devices of the present invention provides features that provide for safer navigation into difficult and sensitive anatomies, and protection of adjacent structures from non-heating threats, the skilled artisan will recognize that these features may also accomplish goals met in some conventional devices as well. For example, when expanded, the expandable intermediate balloon of FIG. 5 may also create a space between the target tissue and the therapeutic agent delivery means, thereby protecting the target tissue from possible overheating.

I claim:

1. A therapeutic probe adapted for insertion between a target tissue and an adjacent tissue, the probe comprising:
   a) a proximal end portion,
   b) a distal end portion,
   c) a longitudinal portion located between the proximal and distal end portions, the longitudinal portion having an axial cross-section defining an outer surface, and
   d) an ultrasound transducer provided in the longitudinal portion and adapted to deliver a therapeutic ultrasound through the outer surface to the target tissue, and
   e) a threadform extending from the outer surface of the longitudinal portion.

2. The probe of claim 1, wherein the threadform comprises an expandable device.

3. The probe of claim 2 wherein the expandable device is adapted to conform to a contour of the adjacent tissue.

4. The probe of claim 2, wherein the expandable device comprises a balloon.

5. The probe of claim 1, wherein the threadform consists essentially of a malleable portion adapted to conform to a contour of the adjacent tissue.

6. The probe of claim 5 wherein the malleable portion comprises a foam portion.

7. The probe of claim 1 wherein the target tissue is intervertebral disc tissue, and the proximal end portion comprises a first expandable portion adapted to conform to a proximal end of the disc tissue.

8. The probe of claim 1 wherein the target tissue is intervertebral disc tissue, and the distal end portion comprises a second expandable portion adapted to conform to a distal end of the disc tissue.

9. A therapeutic probe adapted for insertion between a target tissue and an adjacent tissue, the probe comprising:
   a) a proximal end portion,
   b) a distal end portion,
   c) a longitudinal portion located between the proximal and distal end portions, the longitudinal portion having an axial cross-section defining an outer surface comprising top and bottom surfaces, a front side surface and a back side surface,
   d) ultrasound-delivering means provided in the longitudinal portion and adapted to deliver ultrasound through the front side surface to the target tissue,
   wherein the ultrasound-delivering means comprises a plurality of ultrasound transducers, and
   e) a threadform extending from the outer surface of the longitudinal portion.

* * * * *